US009440908B2

(12) United States Patent
Himmler et al.

(10) Patent No.: US 9,440,908 B2
(45) Date of Patent: Sep. 13, 2016

(54) PROCESS FOR PREPARING N-(5-CHLORO-2-ISOPROPYLBENZYL) CYCLOPROPANAMINE

(71) Applicant: BAYER CROPSCIENCE AG, Monheim (DE)

(72) Inventors: Thomas Himmler, Odenthal (DE); Sandra Lehmann, Leverkusen (DE); Thomas Norbert Muller, Monheim (DE); Mathias Riedrich, Cologne (DE); Lars Rodefeld, Leverkusen (DE); Frank Volz, Cologne (DE); Sascha Von Morgenstern, Burscheid (DE)

(73) Assignee: BAYER CROPSCIENCE AG (DE)

( * ) Notice: Subject to any disclaimer, the term of this patent is extended or adjusted under 35 U.S.C. 154(b) by 0 days.

(21) Appl. No.: 14/396,570

(22) PCT Filed: Apr. 25, 2013

(86) PCT No.: PCT/EP2013/058570
§ 371 (c)(1),
(2) Date: Oct. 23, 2014

(87) PCT Pub. No.: WO2013/160387
PCT Pub. Date: Oct. 31, 2013

(65) Prior Publication Data
US 2015/0094492 A1    Apr. 2, 2015

(30) Foreign Application Priority Data

Apr. 26, 2012  (EP) .................................... 12165663

(51) Int. Cl.
| | | |
|---|---|---|
| *C07C 211/40* | (2006.01) |
| *C07C 209/26* | (2006.01) |
| *C07C 17/093* | (2006.01) |
| *C07C 25/06* | (2006.01) |
| *C07C 45/00* | (2006.01) |
| *C07C 201/12* | (2006.01) |
| *C07C 209/00* | (2006.01) |
| *C07C 209/36* | (2006.01) |
| *C07C 209/70* | (2006.01) |
| *C07C 245/20* | (2006.01) |
| *C07C 249/02* | (2006.01) |
| *C07F 3/02* | (2006.01) |

(52) U.S. Cl.
CPC ........... *C07C 211/40* (2013.01); *C07C 17/093* (2013.01); *C07C 25/06* (2013.01); *C07C 45/004* (2013.01); *C07C 201/12* (2013.01); *C07C 209/00* (2013.01); *C07C 209/26* (2013.01); *C07C 209/365* (2013.01); *C07C 209/70* (2013.01); *C07C 245/20* (2013.01); *C07C 249/02* (2013.01); *C07F 3/02* (2013.01); *C07C 2101/02* (2013.01)

(58) Field of Classification Search
CPC . C07C 17/093; C07C 201/12; C07C 209/00; C07C 209/26; C07C 209/365; C07C 209/70; C07C 2101/02; C07C 211/40; C07C 245/20; C07C 249/02; C07C 25/06; C07C 45/004; C07F 3/02
USPC .......................................... 564/384; 570/182
See application file for complete search history.

(56) References Cited

U.S. PATENT DOCUMENTS

| | | | | |
|---|---|---|---|---|
| 6,242,493 B1 * | 6/2001 | Gareau | .................. | C07C 311/29 |
| | | | | 516/569 |
| 2012/0065164 A1 * | 3/2012 | Bartels | ................. | C07D 231/16 |
| | | | | 514/63 |
| 2013/0217910 A1 * | 8/2013 | Lui | ........................ | C07C 209/52 |
| | | | | 560/48 |
| 2014/0148411 A1 | 5/2014 | Bartels et al. | ................... | 514/63 |

FOREIGN PATENT DOCUMENTS

| | | |
|---|---|---|
| CN | 102421757 A | 4/2012 |
| EP | 2251331 A1 | 11/2010 |
| WO | WO 2012/059585 A1 | 5/2012 |
| WO | WO 2014/076007 * | 5/2014 |

OTHER PUBLICATIONS

National Center for Biotechnology Information. PubChem Compound Database; CID=66158544, https://pubchem.ncbi.nlm.nih.gov/compound/66158544 (accessed Nov. 23, 2015 and first made available online on Oct. 24, 2012—hereafter '544).*
National Center for Biotechnology Information. PubChem Compound Database; CID=67988282, https://pubchem.ncbi.nlm.nih.gov/compound/67988282 (accessed Nov. 23, 2015 and first made available online on Nov. 30, 2012—hereafter '282).*
Overberger ("m-Chlorophenylmethylcarbinol" Organic Syntheses, Coll. vol. 3, p. 200 (1955), vol. 28, p. 28 (1948).*
Obushak ("Arenediazonium Tetrachlorocuprates(II). Modified Versions of the Meerwein and Sandmeyer Reactions" Russian Journal of Organic Chemistry, vol. 38, No. 1, 2002, p. 38-46).*
Crawford ("The Preparation of Some Alkyl-substituted Benzoic Acids" J. Chem. Soc. 1952, 4443).*
Eguchi ("Halogenation Using N-Halogenocompounds. II. Acid Catalyzed Bromination of Aromatic Compounds with 1,3-Dibromo-5,5-dimethylhydantoin" The Chemical Society of Japan, Bull. Chem. Soc. Jpn. 67, 1918-1921, 1994).*
U.S. Appl. No. 13/883,241, filed May 2 2013 by Norbert Lui et al., entitled "Process for the Preparation of Substituted N-(Benzyl)Cyclopropanamines by Imine Hydrogenation".
Office Action issued Dec. 10, 2014 in U.S. Appl. No. 13/883,241.
International Search Report issued Jul. 29, 2013 in corresponding International Application No. PCT/EP2013/058570.
H.T. Nagasawa et al. "Latent Inhibitors of Aldehyde Dehydrogenase as Alcohol Deterrent Agents", J. Med. Chem., 27 (10), pp. 1335-1339, 1984.
Krisztina Vukics et al. "Synthesis of C-Aryl-N-cyclopropylnitrones" Synthetic Communications, vol. 33, No. 19, pp. 3419-3425, 2003.
C.G. Overberger et al. "m-Chlorophenylmethylcarbinol", Organic Syntheses, vol. 28, p. 28 (1948).

* cited by examiner

*Primary Examiner* — Jafar Parsa
*Assistant Examiner* — Amy C Bonaparte
(74) *Attorney, Agent, or Firm* — Ostrolenk Faber LLP

(57) ABSTRACT

The present invention relates to a process for preparing N-(5-chloro-2-isopropylbenzyl)cyclopropanamine by hydrogenation of N-[(5-chloro-2-isopropylphenyl)methylene]cyclopropanamine over specific platinum catalysts.

12 Claims, No Drawings

PROCESS FOR PREPARING N-(5-CHLORO-2-ISOPROPYLBENZYL) CYCLOPROPANAMINE

CROSS-REFERENCE TO RELATED APPLICATION(S)

The present application is a 35 U.S.C. §371 national phase conversion of PCT/EP2013/058570 filed on Apr. 25, 2013, which claims priority of European Application No. 12165663.1 filed on Apr. 26, 2012. Applicants claim priority to each of the foregoing applications. The PCT International Application was published in the English language.

The present invention relates to a process for preparing N-(5-chloro-2-isopropylbenzyl)cyclopropanamine by hydrogenation of N-[(5-chloro-2-isopropylphenyl)methylene]cyclopropanamine over specific platinum catalysts.

Preparative processes for brominating strongly deactivated aromatics such as p-alkyl-substituted nitrobenzenes or nitrobenzene itself are described in the literature. The bromination of p-nitroethylbenzene by means of iron and bromine has been described with very low yields (55% yield of crude product and 34% after distillation) and with long reaction times of over 24 hours (*J. Am. Chem. Soc.* 1950, 72, 2804). The bromination of nitrobenzene by means of iron and bromine is described with a yield of always 60-75% of isolated compound (cf. *Organic Synthesis* 1941, Coll. Vol. 1, 123, ibid. 1928, Vol. 8, 48). A further possible way of brominating deactivated aromatics by means of potassium bromate is known (*J. Org. Chem.* 1981, 46, 2169-2171). However, reactions are problematical from a safety point of view because of the decomposition of potassium bromate in over 70% strength sulphuric acid solution. Furthermore, the bromination of p-nitrotoluene or nitrobenzene by means of N-bromosuccinimide in half-concentrated sulphuric acid is known (*Org. Lett.* 2006, 8, 645-647, *J. Org. Chem.* 1965, 30, 304-306). However, this reaction requires N-bromosuccinimide as brominating reagent. Dimethyldibromohydantoin is found to be significantly more efficient (cf. *Bull. Chem. Soc. Jpn.* 1994, 67, 1918-1921). However, trifluoromethanesulphonic acid, a very expensive reagent, is used here as proton source, which would make an industrial process uneconomical. The use of sulphuric acid as proton source is also described in the same reference. However, dichloromethane, which is a problematical solvent from both an environmental and process engineering point of view, is used as solvent and, in addition, a maximum yield in the bromination of p-nitrotoluene of 84% is achieved. Dibromoisocyanuric acid is also known as brominating reagent for deactivated aromatics (*Organikum*, 22nd edition, Wiley-VCH, pp. 367-368.)

In addition, it is known that p-nitrocumene can be converted into bromonitrocumene using a substoichiometric amount (0.5 equivalents) of silver sulphate (cf. WO 2009/05674, *J. Org. Chem.* 1963, 28, 1917-1919). Furthermore, the desired compound is isolated in a yield of only 18% in WO 2009/055674. Both lead to very high production costs.

The reduction of nitrohaloaromatics is likewise described in the literature. Suitable reducing agents are sodium dithionite (Tietze, Eicher in *Reaktionen und Synthesen*, Thieme Verlag 1981, 136 ff.), sodium sulphide, ammonium sulphide (*Applied Catalysis A: General* 2006, 301, 251-258), sodium disulphide (tin in *Reduction of Nitroarenes, Organic Reactions* (New York), 1973, 20, 455-477), hydrazine hydrate (*Chem. Rev.* 1965, 65, 51-68), iron in combination with mineral acid such as hydrochloric acid, sulphuric acid, acetic acid (*Adv. Synth. Catal.* 2005, 347, 217-219), formic acid or Lewis acids such as iron (II) sulphate (*Org. Synth.* 1955, Coll. Vol. 3, 56; ibid. 1948, Vol. 28, 11), iron(III) chloride (*Ber. dtsch. Chem.* 1927, 1173-1182), aluminium compounds (*J. Chem. Soc. Pak.* 1988, 10, 393-395), platinum catalysts (*Chem. Cat. Chem.* 2009, 1, 210-221; *Synthesis* 2003, 11, 1657-1660: additives such as $ZnX_2$ (X=Cl, Br, I), aluminium(III) chloride, magnesium bromide and copper(I) chloride and copper(II) bromide), Raney nickel (Tietze, Eicher in *Reaktionen und Synthesen*, Thieme Verlag 1981, 466 ff.) and ascorbic acid (*Commun. Fac. Sci. Univ. Ank. Serie B* 1988, 34, 159-162). In addition, it is known in the literature that aromatic nitro compounds can be reduced by means of complex borohydrides such as sodium borohydride, sodium cyanoborohydride, sodium acetoxyborohydride and also aluminates such as lithium aluminium hydride or diisobutylaluminium hydride. Appropriate reaction conditions are known per se to those skilled in the art.

Preparative processes for the chlorination of aromatics by means of the Sandmeyer reaction are described in the literature (e.g. *Organikum* 22nd edition, Wiley-VCH, 640 ff.). The diazotization of 3-bromo-4-isopropylaniline is described in *J. Org. Chem.* 1963, 28, 1917-1919 and *J. Chem. Soc.* 1952, 4443 ff.

The conversion of a bromoaromatic into the corresponding Grignard compound (*J. Org. Chem.* 1963, 28, 1917-1919) and the reaction of this with dimethylformamide to form benzaldehyde (*Synth. Commun.* 1984, 228-230) has been described. The reaction of m-bromochlorobenzene with magnesium, with selective insertion of the magnesium into the C—Br bond, and the subsequent reaction with an electrophile (acetaldehyde) is likewise known (*Org. Synth.* 1955, Coll. Vol. 3, 200; ibid. 1948, Vol. 28, 28).

The reductive amination of benzaldehydes by means of cyclopropylamine is described in PCT/EP2011/069426. Under the conditions described there, the selective hydrogenation without opening of the cyclopropane ring is possible. However, dehalogenation of the corresponding chloroaromatics [cf. formula (II)] occurs as undesirable secondary reaction under the hydrogenation conditions. Furthermore, it is possible to employ a Leukart-Wallach reaction for carrying out the reductive amination (imine reduction by means of formic acid and derivatives, cf. *J. Am. Chem. Soc.* 1936, 58, 1808-1811, ibid. 1950, 72, 3073-3075; *Bull. Chem. Soc. Jap.* 1976, 49, 2485-2490).

Proceeding from this prior art, it is an object of the present invention to provide an alternative process for preparing N-(5-chloro-2-isopropylbenzyl)cyclopropanamine in high purity, yield and better quality without opening of the cyclopropane ring and with simultaneous suppression of the secondary dehalogenation reaction, with the process preferably being simple and inexpensive to carry out. In particular, the process sought should make it possible to obtain the desired target compound without the necessity of a complex purification.

This object is achieved by a novel process for preparing N-(5-chloro-2-isopropylbenzyl)cyclopropanamine.

The present invention relates to a process for preparing N-(5-chloro-2-isopropylbenzyl)cyclopropanamine of the formula (I)

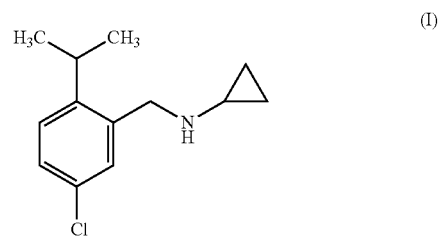

characterized in that
(d) N-[(5-chloro-2-isopropylphenyl)methylene]cyclopropanamine of the formula (III)

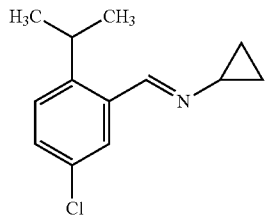
(III)

is hydrogenated over specific platinum catalysts.

The present invention also relates to a process for preparing N-(5-chloro-2-isopropylbenzyl)cyclopropanamine of the formula (I)

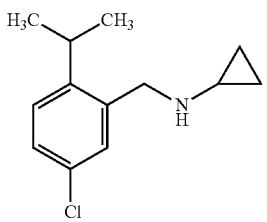
(I)

characterized in that
(c) 5-chloro-2-isopropylbenzaldehyde of the formula (II)

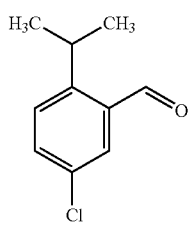
(II)

is reacted with cyclopropylamine in a first step and
(d) the resulting N-[(5-chloro-2-isopropylphenyl)methylene]cyclopropanamine of the formula (III)

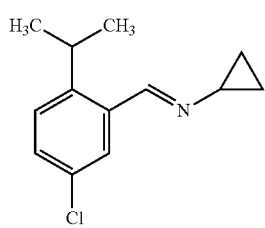
(III)

is hydrogenated over specific platinum catalysts in a second step.

The present invention also relates to a process for preparing N-(5-chloro-2-isopropylbenzyl)cyclopropanamine of the formula (I)

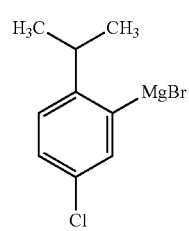
(I)

characterized in that
(b) the Grignard compound of the formula (V)

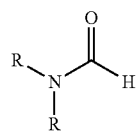
(V)

is react with a dialkylformamide of the formula (VI)

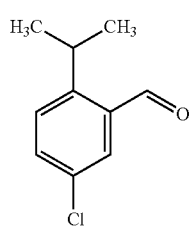
(VI)

where R is independently from each other $C_1$-$C_4$-alkyl, preferably independently methyl or n-butyl, even more preferably methyl, and
(c) the resulting 5-chloro-2-isopropylbenzaldehyde of the formula (II)

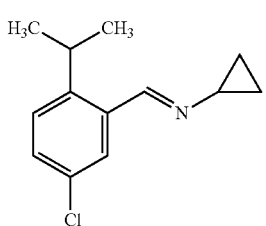
(II)

is reacted with cyclopropylamine, and
(d) the resulting N-[(5-chloro-2-isopropylphenyl)methylene]cyclopropanamine of the formula (III)

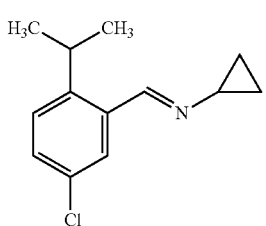
(III)

is hydrogenated over specific platinum catalysts.

The present invention also relates to a process for preparing N-(5-chloro-2-isopropylbenzyl)cyclopropanamine of the formula (I)

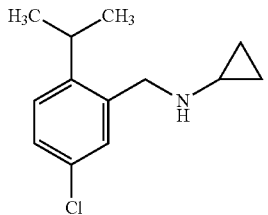
(I)

characterized in that
(a) 2-bromo-4-chloro-1-isopropylbenzene of the formula (IV)

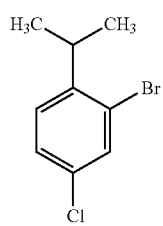
(IV)

is reacted with magnesium with selective insertion of the magnesium into the C—Br bond, and
(b) the resulting Grignard compound of the formula (V)

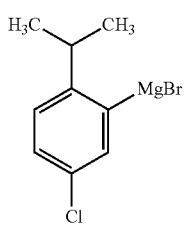
(V)

is reacted with a dialkylformamide of the formula (VI)

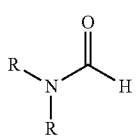
(VI)

where R is independently from each other $C_1$-$C_4$-alkyl, preferably independently methyl or n-butyl, even more preferably methyl, and (c) the resulting 5-chloro-2-isopropylbenzaldehyde of the formula (II)

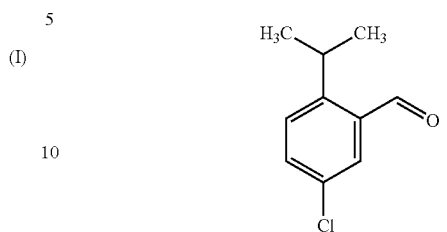
(II)

is reacted with cyclopropylamine, and
(d) the resulting N-[(5-chloro-2-isopropylphenyl)methylene]cyclopropanamine of the formula (III)

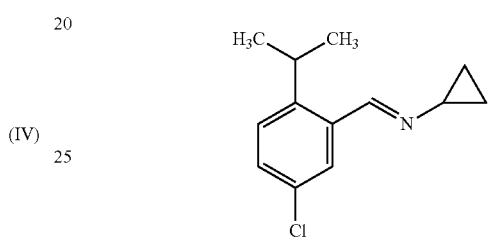
(III)

is hydrogenated over specific platinum catalysts.

N-(5-chloro-2-isopropylbenzyl)cyclopropanamine of the formula (I)

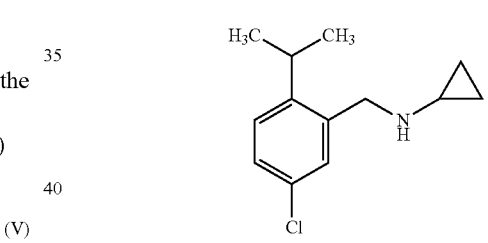
(I)

is new and likewise provided by the present invention.

It has surprisingly been found that the reaction of the benzaldehyde (II) with cyclopropylamine likewise leads to the desired product, even though the aromatic part bears chlorine substituent. Dehalogenations in the hydrogenation of haloaromatics are described in the literature (*J. Org. Chem.* 1977, 42, 3491-3494). In the case of the present invention, this secondary reaction was able to be very largely suppressed.

5-Chloro-2-isopropylbenzaldehyde of the formula (II) is obtained by
(a) reacting 2-bromo-4-chloro-1-isopropylbenzene of the formula (IV)

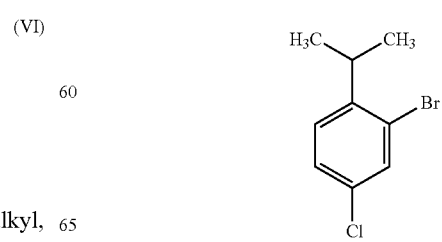
(IV)

with magnesium with selective insertion of the magnesium into the C—Br bond and subsequently (b) reacting the resulting Grignard compound of the formula (V)

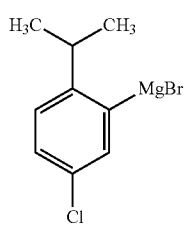

with a dialkylformamide of the formula (VI)

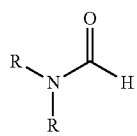

where R is independently $C_1$-$C_4$-alkyl, preferably independently methyl or n-butyl, particularly preferably methyl.

2-Bromo-4-chloro-1-isopropylbenzene of the formula (IV)

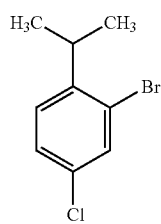

is new and likewise provided by the present invention.

The present invention further relates to the process for preparing 2-Bromo-4-chloro-1-isopropylbenzene of the formula (IV) by (i) react the diazonium salts of the formula (IX)

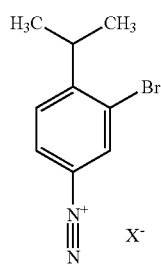

where X is $HSO_4$, Cl, Br, $HCO_2$, $CH_3CO_2$ or $H_2PO_4$ with $CuCl$, $FeCl_2$ or $FeSO_4$ and aqueous HCl or metal chloride, wherein metal is sodium, potassium, caesium, calcium or magnesium.

The present invention further relates to the process for preparing 2-Bromo-4-chloro-1-isopropylbenzene of the formula (IV) by (h) reacting the ammonium salts of the formula (VIII)

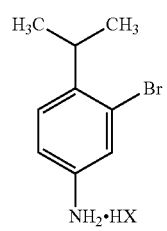

where X is $HSO_4$, Cl, Br, $HCO_2$, $CH_3CO_2$ or $H_2PO_4$ with $NaNO_2$ and/or $KNO_2$ or $C_1$-$C_{20}$-alkyl nitrites, and subsequently (i) reacting the resulting diazonium salts of the formula (IX)

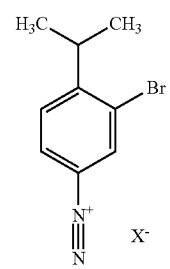

where X is as above defined, with $CuCl$, $FeCl_2$ or $FeSO_4$ and aqueous HCl or metal chloride, wherein metal is sodium, potassium, caesium, calcium or magnesium.

The present invention further relates to the process for preparing 2-Bromo-4-chloro-1-isopropylbenzene of the formula (IV) by (g) firstly converting 3-bromo-4-isopropylaniline of the formula (VII)

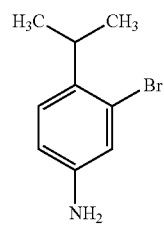

by means of acids (preferably $H_2SO_4$, HCl, HBr, $HCO_2H$, $CH_3CO_2H$ or $H_3PO_4$, particularly preferably $H_2SO_4$ or HCl) into the ammonium salts of the formula (VIII)

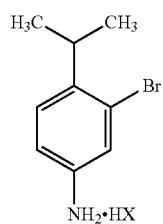
(VIII)

which are then
(h) reacted with NaNO$_2$ and/or KNO$_2$ or C$_1$-C$_{20}$-alkyl nitrites to form the diazonium salts of the formula (IX)

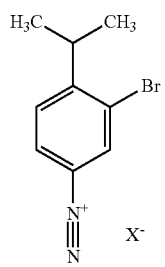
(IX)

(i) which are subsequently reacted with CuCl, FeCl$_2$ or FeSO$_4$ and aqueous HCl or metal chloride, wherein metal is sodium, potassium, caesium, calcium or magnesium.

3-Bromo-4-isopropylaniline of the formula (VII) is obtained by
(e) firstly brominating p-nitrocumene of the formula (X)

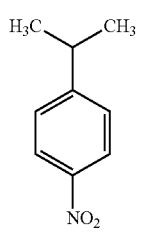
(X)

by means of dimethyldibromohydantoin in sulphuric acid and
(f) reducing the resulting 2-bromo-1-isopropyl-4-nitrobenzene of the formula (XI)

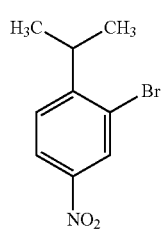
(XI)

The present invention further relates to the process for preparing 2-Bromo-4-chloro-1-isopropylbenzene of the formula (IV) by (f) reducing the resulting 2-bromo-1-isopropyl-4-nitrobenzene of the formula (XI)

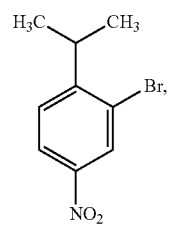
(XI)

and
(g) converting the resulting 3-bromo-4-isopropylaniline of the formula (VII)

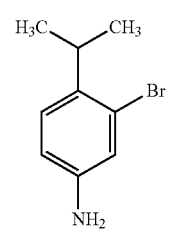
(VII)

by means of acids (preferably H$_2$SO$_4$, HCl, HCO$_2$H, CH$_3$CO$_2$H or H$_3$PO$_4$, particularly preferably H$_2$SO$_4$ or HCl) into the ammonium salts of the formula (VIII)

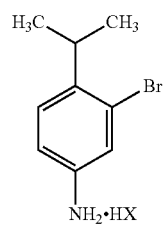
(VIII)

which are then
(h) reacted with NaNO$_2$ and/or KNO$_2$ or C$_1$-C$_{20}$-alkyl nitrites to form the diazonium salts of the formula (IX)

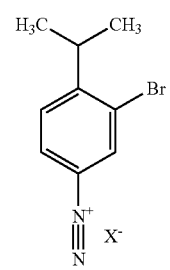
(IX)

(i) which are subsequently reacted with CuCl, FeCl$_2$ or FeSO$_4$ and aqueous HCl or metal chloride, wherein metal is sodium, potassium, caesium, calcium or magnesium, wherein X is as herein defined.

The present invention further relates to the process for preparing 2-Bromo-4-chloro-1-isopropylbenzene of the formula (IV) by
(e) firstly brominating p-nitrocumene of the formula (X)

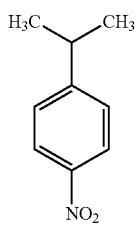
(X)

by means of dimethyldibromohydantoin in sulphuric acid and
(f) reducing the resulting 2-bromo-1-isopropyl-4-nitrobenzene of the formula (XI)

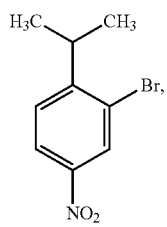
(XI)

and
(g) converting the resulting 3-bromo-4-isopropylaniline of the formula (VII)

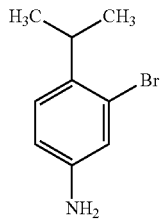
(VII)

by means of acids (preferably H$_2$SO$_4$, HCl, HCO$_2$H, CH$_3$CO$_2$H or H$_3$PO$_4$, particularly preferably H$_2$SO$_4$ or HCl) into the ammonium salts of the formula (VIII)

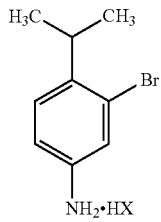
(VIII)

which are then
(h) reacted with NaNO$_2$ and/or KNO$_2$ or C$_1$-C$_{20}$-alkyl nitrites to form the diazonium salts of the formula (IX)

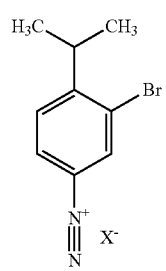
(IX)

(i) which are subsequently reacted with CuCl, FeCl$_2$ or FeSO$_4$ and aqueous HCl or metal chloride, wherein metal is sodium, potassium, caesium, calcium or magnesium, wherein X is as herein defined.

It has surprisingly been found that p-nitrocumene can be brominated in very high yields (>90% chemical yield) in sulphuric acid when dibromohydantoin is slowly introduced. In this mode of operation, the use of organic solvents such as dichloromethane, chloroform or tetrachloromethane can be dispensed with, which is very advantageous from an environmental and process engineering point of view. Interestingly, these reaction conditions work very well for p-nitrocumene, although this substrate is a rather more sterically hindered compound (isopropyl radical in p-nitrocumene) than p-nitrotoluene (methyl radical). In addition, it is possible to brominate p-nitrocumene in high yields (>95%) by means of bromine and catalytic amounts of iron (III) chloride in reaction times of 3-5 hours. Comparable systems (use of iron and bromine to form the system: iron(III) bromide and bromine) applied to comparable substrates (p-nitroethylbenzene) are stated in the literature to give significantly lower yield (55%) and require very long reaction times (>24 hours) (J. Am. Chem. Soc. 1950, 72, 2804).

Substituted N-(benzyl)cyclopropanamines are important intermediates in the preparation of agrochemical active compounds. Appropriately substituted N-(benzyl)cyclopropanamines have been described, for example, in the synthesis of fungicidally active pyrazolecarboxamides (cf., for example, WO 2007/087906, WO 2010/130767).

Thus, for example, N-(5-chloro-2-isopropylbenzyl)cyclopropanamine of the formula (I) can be reacted with pyrazole derivatives of the formula (P1)

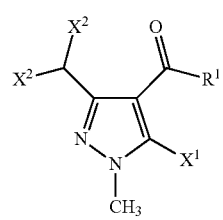
(P1)

where
X$^1$ is fluorine or chlorine (preferably fluorine),
X$^2$ is fluorine or chlorine (preferably fluorine),
R$^1$ is hydroxy, fluorine, chlorine or bromine,
optionally in the presence of a diluent, optionally in the presence of a condensing agent and optionally in the presence of an acid binder, to form pyrazolecarboxylic acids of the formula (P2)

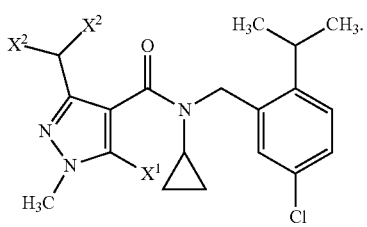

(P2)

Step (c)

The conversion of 5-chloro-2-isopropylbenzaldehyde of the formula (II) into the corresponding N-[(5-chloro-2-isopropylphenyl)methylene]cyclopropanamine of the formula (III) is effected by reaction with cyclopropylamine [process (c)].

In carrying out process (c), an acid can optionally be added as catalyst. Examples are acetic acid, p-toluenesulphonic acid and trifluoroacetic acid. Preference is given to using acetic acid. Acidic salts, e.g. $KHSO_4$ or $NaHSO_4$, can also be used. If appropriate catalysts are used, the amount of these can be from 0.01 to 10 percent by weight, based on the cyclopropylamine used.

Process (c) can also be carried out with the water formed by condensation in the reaction between cyclopropylamine and 5-chloro-2-isopropylbenzaldehyde of the formula (II) being removed from the reaction mixture. This is possible, for example, by use of water-binding agents, for example sodium sulphate, magnesium sulphate or molecular sieves, or by use of an apparatus for removing water. However, the hydrogenation can also be carried out without removal of the water.

Process (c) can generally be carried out under reduced pressure, at atmospheric pressure or under superatmospheric pressure. The temperatures employed can vary as a function of the substrates used and can easily be determined by a person skilled in the art by means of routine tests. For example, the reaction for preparing the compounds of the general formula (I) can be carried out at a temperature of from −20 to +200° C., preferably from +10 to +100° C. The reaction is particularly preferably carried out at atmospheric pressure and temperatures of from +10 to +100° C.

Process (c) can also be carried out in the presence of solvents (diluents). The solvents are preferably also used in this process step in such an amount that the reaction mixture remains readily stirrable during the entire reduction process. Possible solvents for carrying out the process for preparing the imine of the formula (III) are all organic solvents which are inert under the reaction conditions. Examples which may be mentioned are: alcohols such as methanol, ethanol, isopropanol, butanol; ethers such as ethyl propyl ether, methyl tert-butyl ether, n-butyl ether, anisole, phenetole, cyclohexyl methyl ether, dimethyl ether, diethyl ether, dimethyl glycol diphenyl ether, dipropyl ether, diisopropyl ether, di-n-butyl ether, diisobutyl ether, diisoamyl ether, ethylene glycol dimethyl ether, isopropyl ethyl ether, tetrahydrofuran, dioxane, bis(chloroethyl) ether and polyethers of ethylene oxide and/or propylene oxide; nitrohydrocarbons such as nitromethane, nitroethane, nitropropane, nitrobenzene, chloronitrobenzene, o-nitrotoluene; nitriles such as acetonitrile, methylnitrile, propionitrile, butyronitrile, isobutyronitrile, benzonitrile, phenylnitrile, m-chlorobenzonitrile and also compounds such as tetrahydrothiophene dioxide and dimethyl sulphoxide, tetramethylene sulphoxide, dipropyl sulphoxide, benzyl methyl sulphoxide, diisobutyl sulphoxide, dibutyl sulphoxide, diisoamyl sulphoxide; sulphones such as dimethyl sulphone, diethyl sulphone, dipropyl sulphone, dibutyl sulphone, diphenyl sulphone, dihexyl sulphone, methyl ethyl sulphone, ethyl propyl sulphone, ethyl isobutyl sulphone and pentamethylene sulphone; aliphatic, cycloaliphatic or aromatic hydrocarbons such as pentane, hexane, heptane, octane, nonane and industrial hydrocarbons, for example white spirits containing components having boiling points in the range from, for example, 40° C. to 250° C., cymene, petroleum spirit fractions in a boiling range from 70° C. to 190° C., cyclohexane, methylcyclohexane, petroleum ether, ligroin, octane, benzene, toluene, nitrobenzene and xylene. Among the abovementioned solvents, preference is given to methanol, xylene, cyclohexane and particular preference is given to methanol, ethanol, toluene.

In a further embodiment of process (c), the reaction of cyclopropylamine with the carbonyl compound of the formula (II), can also be carried out in bulk.

If the reaction is carried out in a solvent, the solvent can be removed by being distilled off after the end of the reaction. This can be carried out under atmospheric pressure or reduced pressure at room temperature or elevated temperatures. However, the mixture can also be transferred directly to the hydrogenation, which is particularly advantageous for economic reasons. In this embodiment of the process, a work-up of the imine of the formula (III) is then dispensed with. When the imine of the formula (III) is isolated, yields of greater than 95% have been observed.

Step (d)

The reaction of N-[(5-chloro-2-isopropylphenyl)methylene]cyclopropanamine of the formula (III) to form N-(5-chloro-2-isopropylbenzyl)cyclopropanamine of the formula (I) is carried out as a catalytic hydrogenation [process (d)]. In the catalytic hydrogenation to reduce the compound of the formula (III), any hydrogenation catalyst can be used as catalyst. Suitable catalysts optionally contain one or more metals of groups 8-10 of the Periodic Table on any conventional inorganic support. Possibilities are, for example, noble metal catalysts such as ruthenium catalysts, palladium catalysts, platinum catalysts and rhodium catalysts, Raney nickel catalysts and Raney cobalt and Lindlar catalysts. However, apart from these heterogeneous catalysts, hydrogenations can also be carried out over homogeneous catalysts, for example over the Wilkinson catalyst. The corresponding catalysts can also be used in supported form, for example applied to carbon (charcoal or activated carbon), aluminium oxide, silicon dioxide, zirconium dioxide, calcium carbonate or titanium dioxide. Such catalysts are known to those skilled in the art. Particular preference is given to palladium catalysts. The catalysts can be used either moist with water or in dry form. The catalyst used is preferably reused for a plurality of reactions.

In the process, the catalyst is used in a concentration of from about 0.01 to about 30% by weight, based on the imine of the formula (III) used. The catalyst is preferably used in a concentration of from about 0.1 to about 5% by weight, particularly preferably from about 0.1 to about 2.0% by weight.

The catalytic hydrogenation can be carried out under superatmospheric pressure in an autoclave or at atmospheric pressure in a hydrogen gas atmosphere. The hydrogen gas atmosphere can additionally contain inert gases, for example argon or nitrogen. The catalytic hydrogenation is preferably carried out at a temperature of from 10 to 200° C., particularly preferably from 10 to 150° C., very particularly preferably from 10 to 60° C. The hydrogen pressure is usually from 0.1 to 50 bar, preferably from 0.1 to 30 bar, particularly preferably from 1 to 6 bar.

Further reagents and hydrogenation conditions used for the hydrogenation of imines are described in the publications by Harada, in Patai, "The Chemistry of the Carbon-Nitrogen Double Bond", pages 276 to 293; by Nishimura, "Handbook of Heterogeneous Catalytic Hydrogenation for Organic Synthesis", pages 226 to 250, John Wiley and Sons, New York, 2001 and by Rylander, "Catalytic Hydrogenation over Platinum Metals", pages 291 to 303, Academic Press, New York, 1967.

In general, it is advantageous to carry out the process of hydrogenation of the imines in the presence of solvents (diluents). Solvents are advantageously used in such an amount that the reaction mixture remains readily stirrable during the entire process of reduction. Possible solvents for carrying out the process are all organic solvents which are inert under the reaction conditions, with the type of solvents used depending on the way in which the reduction is carried out.

Examples which may be mentioned are alcohols such as methanol, ethanol, isopropanol, butanol; ethers such as ethyl propyl ether, methyl tert-butyl ether, n-butyl ether, anisole, phenetole, cyclohexyl methyl ether, dimethyl ether, diethyl ether, dimethyl glycol diphenyl ether, dipropyl ether, diisopropyl ether, di-n-butyl ether, diisobutyl ether, diisoamyl ether, ethylene glycol dimethyl ether, isopropyl ethyl ether, tetrahydrofuran, methyltetrahydrofuran, dioxane, bis(chloroethyl) ether and polyethers of ethylene oxide and/or propylene oxide; amines such as trimethylamine, triethylamine, tripropylamine, tributylamine, N-methylmorpholine, pyridine, alkylated pyridines and tetramethylenediamine; aliphatic, cycloaliphatic or aromatic hydrocarbons such as pentane, n-hexane, n-heptane, n-octane, nonane and industrial hydrocarbons which can be substituted by fluorine and chlorine atoms, e.g. methylene chloride, dichloromethane, trichloromethane, carbon tetrachloride, fluorobenzene, chlorobenzene or dichlorobenzene; for example white spirits containing components having boiling points in the range from, for example, 40° C. to 250° C., cymene, petroleum spirit fractions in a boiling range from 70° C. to 190° C., cyclohexane, methylcyclohexane, petroleum ether, ligroin, octane, benzene, toluene, chlorobenzene, bromobenzene, nitrobenzene, xylene; esters such as methyl acetate, ethyl acetate, butyl acetate, isobutyl acetate and also dimethyl carbonate, dibutyl carbonate, ethylene carbonate; and aliphatic alcohols such as methanol, ethanol, n-propanol and isopropanol and n-butanol. Among the abovementioned solvents, preference is given to methanol, xylene, cyclohexane and particular preference is given to methanol, ethanol, toluene.

The reaction according to process (d) can be carried out in bulk or without solvents.

The amounts of solvents used in the reaction according to process (d) can be varied in a wide range. In general, the amounts of solvent used are in the range from a 1-fold to 50-fold amount of solvent, particularly preferably from a 2-fold to 40-fold amount of solvent, in particular from a 2-fold to 30-fold amount of solvent, in each case based on the N-[(5-chloro-2-isopropylphenyl)methylene]cyclopropanamine of the formula (III) used.

It has surprisingly been observed that apart from the known reaction, hydrogenolysis of the cyclopropyl substituents is observed to only a small extent in process (d) under the particularly preferred reaction conditions for the process and in addition dehalogenation of the chloroaromatic is also observed to only a small extent.

The work-up (purification) and isolation of the imine of the formula (III) can, for example, be carried out by crystallization and/or distillation.

Step (a)

The conversion of the bromochloro compound of the formula (IV) into the corresponding Grignard compound of the formula (V) is effected by reaction with magnesium [process (a)].

The process (a) is preferably carried out in a temperature range from −80° C. to +120° C., particularly preferably at temperatures of from 10° C. to +70° C.

The process (a) is generally carried out under atmospheric pressure. However, it is also possible as an alternative to work under reduced pressure or under superatmospheric pressure.

The reaction time is not critical and can be selected in a region of one and more hours, depending on the batch size and on the temperature.

When carrying out process (a), from 0.4 mol to 1.8 mol, preferably from 0.9 mol to 1.5 mol, particularly preferably from 1.0 to 1.2 mol, of magnesium is used per mole of the bromochlorocumene of the formula (IV).

After the reaction is complete, the organomagnesium solution obtained can be used directly in the next process step [process (b)]. The Grignard compound is usually formed in quantitative chemical yield. For the subsequent reaction, it is advisable to filter the organomagnesium compound of the formula (V) obtained as a solution in suitable organic solvents.

Suitable solvents for process (a) are, for example, aliphatic, alicyclic or aromatic hydrocarbons such as toluene, o-, m- and p-xylenes, mesitylene, ethers such as ethyl propyl ether, tert-amyl methyl ether, methyl tert-butyl ether, n-butyl ether, anisole, phenetole, cyclohexyl methyl ether, dimethyl ether, diethyl ether, dimethyl glycol diphenyl ether, dipropyl ether, diisopropyl ether, di-n-butyl ether, diisobutyl ether, diisoamyl ether, ethylene glycol dimethyl ether, isopropyl ethyl ether, tetrahydrofuran, methyltetrahydrofuran, dioxane, bis(chloroethyl) ether and polyethers of ethylene oxide and/or propylene oxide. Particular preference is given to using tetrahydrofuran, methyltetrahydrofuran, methyl tert-butyl ether and mixtures of tetrahydrofuran, methyl tetrahydrofuran, methyl tert-butyl ether with toluene and/or xylenes. The amounts of solvents used in the reaction according to process (a) can be varied in a wide range. In general, the amounts of solvents used are in the range from a 1-fold to 50-fold amount of solvent, particularly preferably from a 2-fold to 40-fold amount of solvent, in particular from a 2-fold to 30-fold amount of solvent, in each case based on the bromochlorocumene of the formula (IV) used.

Step (b)

The conversion of the Grignard compound of the formula (V) into the corresponding 5-chloro-2-isopropylbenzaldehyde of the formula (II) is effected by reaction with dialkylformamides of the formula (VI) [process (b)].

The process (b) is preferably carried out in a temperature range from 80° C. to +120° C., particularly preferably at temperatures of from −10° C. to +70° C.

The process (b) is generally carried out under atmospheric pressure. However, it is also possible as an alternative to work under reduced pressure or under superatmospheric pressure.

The reaction time is not critical and can be selected in the region of one and more hours, depending on the batch size and on the temperature.

When carrying out process (b), from 1.0 mol to 5.0 mol, preferably from 1.0 mol to 2 mol, particularly preferably from 1.0 to 1.5 mol, of dialkylformamide of the formula (VI) is used per mol of the Grignard compound of the formula (V).

After the reaction is complete, the reaction solution obtained can be admixed with aqueous mineral acids. 5-Chloro-2-isopropylbenzaldehyde of the formula (II) is formed in yields of 85-95% of the chemical yield.

Suitable solvents for the process (b) are, for example, aliphatic, alicyclic or aromatic hydrocarbons such as toluene, o-, m- and p-xylenes, mesitylene, ethers such as ethyl propyl ether, tert-amyl methyl ether, methyl tert-butyl ether, n-butyl ether, anisole, phenetole, cyclohexyl methyl ether, dimethyl ether, diethyl ether, dimethyl glycol diphenyl ether, dipropyl ether, diisopropyl ether, di-n-butyl ether, diisobutyl ether, diisoamyl ether, ethylene glycol dimethyl ether, isopropyl ethyl ether, tetrahydrofuran, methyltetrahydrofuran, dioxane, bis(chloroethyl) ether and polyethers of ethylene oxide and/or propylene oxide. Particular preference is given to using tetrahydrofuran, methyltetrahydrofuran, methyl tert-butyl ether ether and mixtures of tetrahydrofuran, methyltetrahydrofuran, methyl tert-butyl ether with toluene and/or xylenes. The amounts of solvents used in the reaction according to process (b) can be varied in a wide range. In general, the amounts of solvent used are in the range from a 1-fold to 50-fold amount of solvent, particularly preferably from a 2-fold to 40-fold amount of solvent, in particular from a 2-fold to 30-fold amount of solvent, in each case based on the Grignard compound of the formula (V) used.

Step g:

The conversion of the aniline compound of the formula (VII) into the corresponding ammonium salts of the formula (VIII) is effected by reaction with mineral acids and/or organic acids [process (g)].

The process (g) is preferably carried out in a temperature range from −30° C. to +120° C., particularly preferably at temperatures of from −10° C. to +70° C.

The process (g) is generally carried out under atmospheric pressure. However, it is also possible, as an alternative, to work under reduced pressure or under superatmospheric pressure.

The reaction time is not critical and can be selected in the region of one and more hours, depending on the batch size and on the temperature.

When carrying out the process (g), from 1.0 mol to 5.0 mol, preferably from 1.0 mol to 4.0 mol, particularly preferably from 1.0 to 3.0 mol of acids ($H_2SO_4$, HCl, HBr, $HCO_2H$, $CH_3CO_2H$, $H_3PO_4$, particularly preferably $H_2SO_4$, HCl) is used per mol of the aniline compound of the formula (VII).

Suitable solvents for process (g) are water, alcohols such as methanol, ethanol, isopropanol, butanol; ethers such as ethyl propyl ether, methyl tert-butyl ether, n-butyl ether, anisole, phenetole, cyclohexylmethyl ether, dimethyl ether, diethyl ether, dimethyl glycol diphenyl ether, dipropyl ether, diisopropyl ether, di-n-butyl ether, diisobutyl ether, diisoamyl ether, ethylene glycol dimethyl ether, isopropyl ethyl ether, tetrahydrofuran, methyltetrahydrofuran, dioxane, bis(chloroethyl) ether and polyethers of ethylene oxide and/or propylene oxide; aliphatic, cycloaliphatic or aromatic hydrocarbons such as pentane, n-hexane, n-heptane, n-octane, nonane and industrial hydrocarbons which may be substituted by fluorine and chlorine atoms, e.g. methylene chloride, dichloromethane, trichloromethane, carbon tetrachloride, fluorobenzene; for example white spirits containing components having boiling points in the range from, for example, 40° C. to 250° C., cymene, petroleum spirit fractions in a boiling range from 70° C. to 190° C., cyclohexane, methylcyclohexane, petroleum ether, ligroin, octane, benzene, toluene, chlorobenzene, dichlorobenzene, bromobenzene, nitrobenzene, xylene; esters such as methyl acetate, ethyl acetate, butyl acetate, isobutyl acetate and also dimethyl carbonate, dibutyl carbonate, ethylene carbonate; and aliphatic alcohols such as methanol, ethanol, n-propanol and isopropanol and n-butanol. Among the abovementioned solvents, preference is given to alcohols, in particular methanol, ethanol, and water, especially water.

After the reaction is complete, the reaction solution obtained can be subjected directly to diazotization. The ammonium salts are usually formed in quantitative chemical yield.

Step (h)

The conversion of the ammonium salts of the formula (VIII) into the corresponding diazonium salts (IX) is effected by reaction with nitrites ($NaNO_2$ and/or $KNO_2$ or C1-C20-alkyl nitrites, particularly preferably with $NaNO_2$ and/or $KNO_2$) [process (h)].

Process (h) is preferably carried out in a temperature range from −30° C. to +80° C., particularly preferably at temperatures of from −10° C. to +50° C.

The process (h) is generally carried out under atmospheric pressure. However, it is also possible as an alternative to work under reduced pressure or under superatmospheric pressure.

The reaction time is not critical and can be selected in the region of one or more hours, depending on the batch size and on the temperature.

When carrying out the process (h), from 1.0 mol to 5.0 mol, preferably from 1.0 mol to 2 mol, particularly preferably from 1.0 to 1.5 mol, of nitrites ($NaNO_2$ and/or $KNO_2$ or C1-C20-alkyl nitrites, particularly preferably with $NaNO_2$ and/or $KNO_2$) is used per mol of the ammonium salts of the formula (VIII).

After the reaction is complete, the reaction solution obtained can be subjected directly to conversion into the corresponding 2-bromo-4-chloro-1-isopropylbenzene of the formula (IV). The diazonium salts of the formula (IX) are usually formed in quantitative chemical yield.

Suitable solvents for the process (h) are water, organic acids such as acetic acid, propionic acid, trifluoroacetic acid or in mixtures of organic acids with water or in a 2-phase system with organic solvents such as ethers, e.g. ethyl propyl ether, methyl tert-butyl ether, n-butyl ether, cyclohexyl methyl ether, dimethyl ether, diethyl ether, dimethyl glycol diphenyl ether, dipropyl ether, diisopropyl ether, di-n-butyl ether, diisobutyl ether, diisoamyl ether, ethylene glycol dimethyl ether, isopropyl ethyl ether, tetrahydrofuran, methyltetrahydrofuran, dioxane, bis(chloroethyl) ether and polyethers of ethylene oxide and/or propylene oxide; aliphatic, cycloaliphatic or aromatic hydrocarbons such as pentane, n-hexane, n-heptane, n-octane, nonane and industrial hydrocarbons which may be substituted by fluorine and chlorine atoms, e.g. methylene chloride, dichloromethane, trichloromethane, carbon tetrachloride, fluorobenzene; for example white spirits containing components having boiling points in the range from, for example, 40° C. to 250° C., cymene, petroleum spirit fractions in a boiling range from 70° C. to 190° C., cyclohexane, methylcyclohexane, petroleum ether, ligroin, octane, chlorobenzene, dichlorobenzene, bromobenzene, nitrobenzene; esters such as methyl acetate, ethyl acetate, butyl acetate, isobutyl acetate and also dimethyl carbonate, dibutyl carbonate, ethylene carbonate. Among the abovementioned solvents, preference is given to mixtures of water with organic acids and particular preference is given to water. The amounts of solvents used in the reaction according to process (h) can be varied in a wide range. In general, the amounts of solvents used are in the range from a 1-fold to 50-fold amount of solvent, particularly preferably from a 2-fold to 40-fold amount of solvent, in particular from a 2-fold to 30-fold amount of solvent, in each case based on the ammonium salts of the formula (VIII) used.

Step (i)

The conversion of the diazonium salts of the formula (IX) into the corresponding 2-bromo-4-chloro-1-isopropylbenzene of the formula (IV) is effected by reaction with copper (I) chloride and/or copper (II) chloride or iron (II) sulphate, iron (II) chloride or sodium chloride or potassium chloride or mixtures of the aforementioned acids with hydrochloric acid, particularly preferably with copper (I) chloride, iron (II) chloride or iron (II) sulphate in combination with aqueous hydrochloric acid [process (i)].

Process (i) is preferably carried out in a temperature range from −30° C. to +80° C., particularly preferably at temperatures of from −10° C. to +50° C.

The process (i) is generally carried out under atmospheric pressure. However, it is also possible as an alternative to work under reduced pressure or under superatmospheric pressure.

The reaction time is not critical and can be selected in the region of one or more hours, depending on the batch size and on the temperature.

When carrying out the process (i), from 1.0 mol to 5.0 mol, preferably from 1.0 mol to 2 mol, particularly preferably from 1.0 to 1.5 mol, of copper (I) chloride and/or copper (II) chloride, iron (II) chloride or iron (II) sulphate or sodium chloride or potassium chloride or mixtures of the aforementioned salts are used per mol of diazonium salts of the formula (IX).

When carrying out the process (i), from 1.0 mol to 5.0 mol, preferably 1.0 mol to 2 mol, particularly preferably from 1.0 mol to 1.5 mol of aqueous HCl are used per mol of the diazonium salt of the formula (IX).

Suitable solvents for the process (i) are water, organic acids such as acetic acid, propionic acid, trifluoroacetic acid or in mixtures of organic acids with water or in a 2-phase system with organic solvents such as ethers, e.g. ethyl propyl ether, methyl tert-butyl ether, n-butyl ether, cyclohexyl methyl ether, dimethyl ether, diethyl ether, dimethyl glycol diphenyl ether, dipropyl ether, diisopropyl ether, di-n-butyl ether, diisobutyl ether, diisoamyl ether, ethylene glycol dimethyl ether, isopropyl ethyl ether, tetrahydrofuran, methyltetrahydrofuran, dioxane, bis(chloroethyl) ether and polyethers of ethylene oxide and/or propylene oxide; aliphatic, cycloaliphatic or aromatic hydrocarbons such as pentane, n-hexane, n-heptane, n-octane, nonane and industrial hydrocarbons which may be substituted by fluorine and chlorine atoms, e.g. methylene chloride, dichloromethane, trichloromethane, carbon tetrachloride, fluorobenzene; for example white spirits containing components having boiling points in the range from, for example, 40° C. to 250° C., cymene, petroleum spirit fractions in a boiling range from 70° C. to 190° C., cyclohexane, methylcyclohexane, petroleum ether, ligroin, octane, chlorobenzene, dichlorobenzene, bromobenzene, nitrobenzene; esters such as methyl acetate, ethyl acetate, butyl acetate, isobutyl acetate and also dimethyl carbonate, dibutyl carbonate, ethylene carbonate. Among the abovementioned solvents, preference is given to mixtures of water with organic acids and particular preference is given to water. The amounts of solvents used in the reaction according to process (i) can be varied in a wide range. In general, the amounts of solvents used are in the range from a 1-fold to 50-fold amount of solvent, particularly preferably from a 2-fold to 40-fold amount of solvent, in particular from a 2-fold to 30-fold amount of solvent, in each case based on the diazonium salts of the formula (IX) used.

After the reaction is complete, the 2-bromoo-4-chloro-1-isopropylbenzene of the formula (IV) can be extracted. This gives 2-bromo-4-chloro-1-isopropylbenzene of the formula (IV) in chemical yields of about 60-92%.

Step (e)

The bromination of p-nitrocumene of the formula (X) to form the corresponding 2-bromo-1-isopropyl-4-nitrobenzene of the formula (XI) is effected by reaction with brominating reagents such as N-bromosuccinimide, dimethyldibromohydantoin, dibromocyanuric and tribromocyanuric acid in sulphuric acid, bromine, bromine and Lewis acids such as iron(III) chloride, iron(III) bromide, aluminium(III) chloride, aluminium(III) bromide, titanium(IV) chloride [process (e)].

The process (e) is preferably carried out in a temperature range from −20° C. to +120° C., particularly preferably at temperatures of from −10° C. to +40° C.

The process (e) is generally carried out under atmospheric pressure. However, it is also possible as an alternative to work under reduced pressure or under superatmospheric pressure.

The reaction time is not critical and can be selected in the region of one and more hours, depending on the batch size and on the temperature.

When carrying out the process (e), from 0.4 mol to 1.4 mol, preferably from 0.9 mol to 1.2 mol, particularly preferably from 0.50 to 0.65 mol, of dimethyldibromohydantoin or 0.4-2 mol of bromine with 0.01-1 mol of iron(III) chloride, preferably 0.8-1.7 mol of bromine with 0.05-0.8 mol of iron(III) chloride, particularly preferably 0.8-1.4 mol of bromine with 0.1-0.5 mol of iron(III) chloride, is used per mol of p-nitrocumene of the formula (X).

When carrying out the process (e), in the case of dibromohydantoin from 1 mol to 6 mol, preferably from 1.5 mol to 4 mol, particularly preferably from 2 to 3.5 mol, of sulphuric acid are used per mol of p-nitrocumene of the formula (X), and in the case of bromine with iron(III) chloride, the reaction is carried out in chlorinated aliphatic and/or aromatic hydrocarbons, particularly preferably without solvent.

The reaction of process (e) can be carried out in bulk without solvent, which leads to an improved space yield.

After the reaction is complete, the sulphuric acid can be separated off by phase separation and optionally be reused. The crude 2-bromo-1-isopropyl-4-nitrobenzene of the formula (XI) is, for example, washed with aqueous sodium hydroxide solution, potassium hydroxide solution, sodium carbonate or potassium carbonate and obtained in yields of 88-95%. In the case of bromine/iron(III) chloride, the mixture is admixed with water and subsequently extracted with organic solvents. The 2-bromo-1-isopropyl-4-nitrobenzene of the formula (XI) obtained in this way is obtained in very good yield (>90%) and purity without further work-up.

Process (e) can also be carried out in the presence of a solvent. Suitable solvents are, for example, aliphatic, alicyclic or aromatic halogenated hydrocarbons, e.g. chlorobenzene, dichlorobenzene, dichloromethane, chloroform, tetrachloromethane, dichloroethane or trichloroethane, nitriles such as acetonitrile, propionitrile, n-butyronitrile or isobutyronitrile or benzonitrile and water and aliphatic, alicyclic carboxylic acids. Particular preference is given to using chlorobenzene, dichlorobenzene, dichloromethane, chloroform, dichloroethane, trichlorethane, acetic acid, propionic acid, butanoic acid, acetonitrile, butyronitrile and water.

Step (f)

The conversion of the bromonitrocumene of the formula (XI) into the corresponding 3-bromo-4-isopropylaniline of the formula (VII) is effected by reaction with catalysts and hydrogen [process (f)].

Any hydrogenation catalyst can be used as catalyst for the catalytic hydrogenation to reduce the bromonitrocumene of the formula (XI). Suitable catalysts optionally contain one or more metals of groups 8-10 of the Periodic Table on any conventional inorganic support. Possibilities are, for example, noble metal catalysts such as ruthenium catalysts, palladium catalysts, platinum catalysts and rhodium catalysts, Raney nickel catalysts and Raney cobalt and Lindlar catalysts. However, apart from these heterogeneous catalysts, hydrogenations can also be carried out over homogeneous catalysts, for example over the Wilkinson catalyst. The corresponding catalysts can also be used in supported form, for example supported on carbon (charcoal or activated carbon), aluminium oxide, silicon dioxide, zirconium dioxide, calcium carbonate or titanium dioxide. Such catalysts are known per se to those skilled in the art. Particular preference is given to palladium and platinum catalysts with or without addition of Lewis acids such as $ZnX_2$ (X=Cl, Br, I), aluminium(III) chloride, magnesium bromide and copper (I) chloride and copper(II) bromide. The catalysts can be used both moist with water and in dry form. The catalyst used is preferably reused for a plurality of reactions.

In process (f), the catalyst is used in a concentration of from about 0.01 to about 30% by weight, based on the bromonitrocumene of the formula (XI) used. The catalyst is preferably used in a concentration of from about 0.1 to about 5% by weight, particularly preferably from about 0.1 to about 2.0% by weight.

The catalytic hydrogenation can be carried out under superatmospheric pressure in an autoclave or at atmospheric pressure in a hydrogen gas atmosphere. The hydrogen gas atmosphere can additionally contain inert gases, for example argon or nitrogen. The catalytic hydrogenation is preferably carried out at a temperature of from 10 to 200° C., particularly preferably from 10 to 150° C., very particularly preferably from 10 to 60° C. The hydrogen pressure is usually from 0.1 to 50 bar, preferably from 0.1 to 30 bar, particularly preferably from 1 to 6 bar.

It is generally advantageous to carry out the process of hydrogenation of bromonitrocumene of the formula (XI) in the presence of solvents (diluents). Solvents are advantageously used in such an amount that the reaction mixture remains readily stirrable during the entire process of reduction. Possible solvents for carrying out the process are all organic solvents which are inert under the reaction conditions, with the type of solvent used depending on the way in which the reduction is carried out.

The reduction can also be carried out using reducing agents such as sodium dithionite, sodium sulphide, ammonium sulphide, sodium disulphide, hydrazine hydrate (*Chem. Rev.* 1965, 65, 51-68), iron in combination with mineral acid such as hydrochloric acid, sulphuric acid, acetic acid, formic acid or Lewis acids such as iron(II) sulphate, iron(III) chloride, aluminium compounds and also complex borohydrides such as example: sodium borohydride, sodium cyanoborohydride, sodium acetoxyborohydride and aluminates such as lithium aluminium hydride or diisobutylaluminium hydride. Preference is given to sodium sulphide, sodium disulphide and iron with hydrochloric acid. Particular preference is given to sodium sulphide and sodium disulphide.

The process (f) is preferably carried out in a temperature range from −30° C. to +150° C., particularly preferably at temperatures of from 20° C. to +100° C.

The reaction time is not critical and it can be selected in the region of one and more hours, depending on the batch size and on the temperature.

When carrying out the process (f), from 1.0 mol to 5.0 mol of sodium sulphide and/or sodium disulphide, preferably from 1.0 mol to 3.0 mol of sodium sulphide and/or sodium disulphide, particularly preferably from 1.0 to 2.0 mol of sodium sulphide and/or sodium disulphide, are used per mol of the bromonitrocumene of the formula (XI).

Suitable solvents for the process (f) are mixtures of alcohols such as methanol, ethanol, isopropanol, butanol and water; ethers such as ethyl propyl ether, methyl tert-butyl ether, n-butyl ether, anisole, phenetole, cyclohexyl methyl ether, dimethyl ether, diethyl ether, dimethyl glycol diphenyl ether, dipropyl ether, diisopropyl ether, di-n-butyl ether, diisobutyl ether, diisoamyl ether, ethylene glycol dimethyl ether, isopropyl ethyl ether, tetrahydrofuran, methyltetrahydrofuran, dioxane, bis(chloroethyl) ether and polyethers of ethylene oxide and/or propylene oxide; aliphatic, cycloaliphatic or aromatic hydrocarbons such as pentane, n-hexane, n-heptane, n-octane, nonane and industrial hydrocarbons which may be substituted by fluorine and chlorine atoms, e.g. methylene chloride, dichloromethane, trichloromethane, carbon tetrachloride, fluorobenzene; for example white spirits containing components having boiling points in the range from, for example, 40° C. to 250° C., cymene, petroleum spirit fractions in a boiling range from 70° C. to 190° C., cyclohexane, methylcyclohexane, petroleum ether, ligroin, octane, benzene, toluene, chlorobenzene, dichlorobenzene, bromobenzene, nitrobenzene, xylene; esters such as methyl acetate, ethyl acetate, butyl acetate, isobutyl acetate and also dimethyl carbonate, dibutyl carbonate, ethylene carbonate; and aliphatic alcohols such as methanol, ethanol, n-propanol and isopropanol and n-butanol. Among the abovementioned solvents, preference is given to alcohols, in particular methanol, ethanol, isopropanol in admixture with water. The amounts of solvents used in the reaction according to process (i) can be varied in a wide range. In general, the amounts of solvents used are in the range from a 1-fold to 50-fold amount of solvent, particularly preferably from a 2-fold to 40-fold amount of solvent, in particular from a 2-fold to 30-fold amount of solvent, in each case based on the bromonitrocumene of the formula (XI) used.

After the reaction is complete, 3-bromo-4-isopropylaniline of the formula (VII) can be extracted. This gives 3-bromo-4-isopropylaniline of the formula (VII) in chemical yields of about 60-85%.

The present invention further provides for the use of the compounds of the formulae (II) to (XI) for preparing the compound of the formula (I).

PREPARATIVE EXAMPLES

Example 1

2-Bromo-1-isopropyl-4-nitrobenzene of the formula (XI)

1,3-Dibromo-5,5-dimethylhydantoin (86.9 g, 0.298 mol) was added in about 5 g portions to a solution of p-nitrocumene (X) (100 g, 0.581 mol, GC purity 96%) and sulphuric acid (178 g, 1.743 mol, 98% strength) over a period of 5 hours. The mixture was then warmed to room temperature and stirred for another 1 hour. The reaction mixture was poured onto 200 g of ice water and admixed with sodium bisulphite (15.1 g, 0.06 mol) and toluene (300 g). The phases were then separated. The organic phase was washed with 5% strength aqueous sodium hydroxide and the toluene was distilled off under reduced pressure. 2-Bromo-1-isopropyl-4-nitrobenzene (147 g, 93.6 GC-% by area, 97% of theory) was obtained as a pale yellow oil.

A solution of p-nitrocumene (X) (50 g, 0.300 mol, GC purity: 99.1%) and iron(III) chloride was heated to 40° C. and bromine (59.92 g, 0.375 mol) was added dropwise over a period of 3 hours. The reaction mixture was poured into 120 ml of water, sodium hydrogensulphite (40% strength in water, 20.81 g, 0.078 mol) was added dropwise and the mixture was extracted with 100 ml of chlorobenzene. After phase separation, the chlorobenzene phase was washed with 100 ml of 5% strength aqueous HCl. Removal of the chlorobenzene under reduced pressure gave 2-bromo-1-isopropyl-4-nitrobenzene (74.05 g, 96.9 GC-% by area, 98% of theory) as a yellow oil.

$^1$H-NMR (600 MHz, CDCl$_3$): δ=8.41 (d, 1H), 8.14 (dd, 1H), 7.45 (d, 1H), 3.45 (heptet, 1H), 1.29 (d, 3H), 1.27 (d, 3H) ppm.

GC-MS: m/ez=245 [M$^+$].

Example 2

3-Bromo-4-Isopropylaniline of the Formula (VII)

A solution of sodium sulphide (31.2 g, 0.24 mol) and sulphur (7.7 g, 0.24 mol) was stirred at 80° C. for 15 minutes. Isopropanol (160 g) was subsequently added and the mixture was stirred at 75° C. for a further 15 minutes and 2-bromo-1-isopropyl-4-nitrobenzene (XI) (50 g, 0.19 mol) was finally added dropwise over a period of 30 minutes. After stirring for another 5 hours, the reaction was complete. For the work-up, the isopropanol was firstly distilled off and the remaining mixture was extracted with toluene/chlorobenzene. The combined organic phases were distilled under reduced pressure. 3-Bromo-4-isopropylaniline (42 g, 91 GC-% by area, 93% of theory) was obtained as a red oil.

2-Bromo-1-isopropyl-4-nitrobenzene (XI) (20 g, 79.1 mmol, 96.5 GC % by area), methanol 400 ml), platinum on carbon (1% of platinum, 2% of vanadium, moist with water) (1.0 g, 0.018 mmol) and zinc dibromide (90 mg, 0.40 mmol) were placed in a 600 ml autoclave. The autoclave was subsequently flushed with nitrogen and pressurized to 5 bar with hydrogen at room temperature. The contents of the autoclave were filtered through Celite, washed with methanol and the solvent was distilled off under reduced pressure. 3-Bromo-4-isopropylaniline (17.1 g, 93 LC-% by area, 98.3 GC-% by area, 98% of theory) was obtained as a brown oil.

2-Bromo-1-isopropyl-4-nitrobenzene (XI) (20 g, 78.1 mmol, 95.8 GC % by area), methanol (400 ml), platinum on carbon (5% of platinum, poisoned with sulphur, moist with water) (1.0 g, 0.090 mmol) and zinc dibromide (265 mg, 1.18 mmol) were placed in a 600 ml autoclave. The autoclave was subsequently flushed with nitrogen and pressurized to 5 bar with hydrogen at room temperature. The contents of the autoclave were filtered through Celite, washed with methanol and the solvent was distilled off under reduced pressure. 3-Bromo-4-isopropylaniline (17.4 g, 94.5 LC-% by area, 97.7 GC-% by area, >99% of theory) was obtained as a brown oil.

3-Bromo-4-Isopropylaniline of the Formula (VII)

$^1$H-NMR (600 MHz, (CDCl$_3$): δ=7.04 (d, 1H), 6.89 (d, 1H), 6.61 (dd, 1H), 3.56 (br s, 2H), 3.25 (heptet, 1H), 1.19 (s, 3H), 1.18 (s, 3H) ppm.

GC-MS: m/e=213 [M$^+$].

2-Bromo-1-isopropyl-4-nitrobenzene (XI) (50 g, 0.192 mol, 93.5 GC-% by area), 100 ml of water, ironpowder (40.71 g, 0.718 mol) were heated to 70° C. and hydrochloric acid (193.7 g, 1.647 mol, 31% in water) was added over a period of 2 hours. The mixture was then cooled to 0° C. and the suspension was filtered with suction. The solvent obtained was dried overnight at 50° C. in a vacuum drying oven. 3-Bromo-4-isopropylaniline hydrochloride (48 g, purity: 88.7%, contains: 8.6% of iron, 88.7% of theory) was obtained as a light-brown solid.

3-Bromo-4-isopropylaniline hydrochloride of the Formula (VIII)

$^1$H-NMR (600 MHz, d$^4$-MeOD): δ=7.62 (d, 1H), 7.52 (d, 1H), 7.38 (dd, 1H), 4.83 (bs, 2H), 3.40 (heptet, 1H), 1.26 (s, 3H), 1.25 (s, 3H) ppm.

Example 3

2-Bromo-4-chloro-1-isopropylbenzene of the Formula (IV)

Hydrochloric acid (152 g, 31% strength, 1.29 mol) was added dropwise to a suspension of 3-bromo-4-isopropylaniline (VII) (100 g, 0.43 mol) and water (150 g) at room temperature. The suspension was subsequently cooled to 5° C. and a solution of sodium nitrite (32.7 g, 0.46 mol) in water (140 g) was added dropwise over a period of 2 hours. After stirring for another 1 hour, amidosulphuric acid (2.5 g, 0.026 mol) was added. Copper(I) chloride (10.8 g, 0.11 mol), hydrochloric acid (202 g, 31%, 1.72 mol) and water (75 g) were placed in a second flask and the diazonium salt generated previously was added dropwise over a period of 30 minutes. After stirring for another 1.5 hours, the mixture was extracted with dichloromethane (250 g), the phases were separated and dichloromethane was distilled off under reduced pressure. The crude product obtained was purified by distillation. 2-Bromo-4-chloro-1-isopropylbenzene (62.6 g, 94.8 GC-% by area. 59% of theory) was obtained as a colourless oil.

$^1$H-NMR (600 MHz, CDCl$_3$): δ=7.54 (d, 1H), 7.24 (dd, 1H), 7.19 (d, 1H), 3.32 (heptett, 1H), 1.22 (s, 3H), 1.21 (s, 3H) ppm.

GC-MS: m/z=234 [M+H]$^+$.

Example 4

5-Chloro-2-isopropylbenzaldehyde of the Formula (II)

Magnesium (4.6 g, 0.189 mol) together with tetrahydrofuran (65 ml) were placed in a reaction vessel and heated while stirring to 40° C. About 5% of a solution of 2-bromo-4-chloro-1-isopropylbenzene (IV) (43 g, 0.180 mol) in tetrahydrofuran (95 ml) is then added dropwise. After the reaction has commenced, the remainder of the 2-bromo-4-chloro-1-isopropylbenzene in tetrahydrofuran was added under gentle reflux over a period of 1 hour. The mixture was then cooled to 0° C. and dimethylformamide (13.8 g. 0.189 mol) was added dropwise over a period of 1 hour. The reaction mixture obtained was stirred for another 1 hour and hydrochloric acid (86.7 g, 0.369 mol) was added in such a way that the temperature was kept below 30° C. The phases were then separated and extracted with toluene (2×50 ml). The combined organic phases were distilled under reduced pressure and the crude product obtained was recrystallized from isopropanol/water 4:1. 5-Chloro-2-isopropylbenzaldehyde (25.7 g, 99 GC-% by area, 77% of theory) was obtained as a colourless solid.

$^1$H-NMR (600 MHz, CDCl$_3$): δ=10.3 (s, 1H), 7.78 (d, 1H), 7.50 (dd, 1H), 7.39 (d, 1H), 3.89 (hept., 1H), 1.31 (s, 3H), 1.29 (s, 3H) ppm.

GC-MS: m/e=182 [M$^+$].

Example 5

N-[(5-Chloro-2-isopropylphenyl)methylene]cyclopropanamine of the Formula (III)

Cyclopropylamine (39.2 g, 0.69 mol) was added to a solution of 5-chloro-2-isopropylbenzaldehyde (II) (120 g, 0.65 mol, 99.6 GC-% by area) in methanol (1200 ml) and the mixture was stirred at room temperature for 2 hours. The solvent was subsequently removed under reduced pressure and N-[(5-chloro-2-isopropylphenyl)-methylene]cyclopropanamine (144 g, 99.2 GC-% by area, 98.5% of theory) was obtained as a light-yellow oil.

$^1$H-NMR (600 MHz, CDCl$_3$): δ=8.87 (s, 1H), 7.69 (t, 1H), 7.34 (d, 2H), 3.48 (hept., 1H), 1.15 (m, 1H), 1.26 (s, 3H), 1.25 (s, 3H), 0.95 (m, 4H) ppm.

GC-MS: m/e=221 [M$^+$].

The imine obtained in this way can be isolated as described above. As an alternative, it is left in the respective solvent, the catalyst is added and hydrogen is injected, which is described below:

Example 6

N-(5-Chloro-2-isopropylbenzyl)cyclopropanamine of the Formula (I)

Cyclopropylamine (3.26 g, 0.057 mol) was added to a solution of 5-chloro-2-isopropylbenzaldehyde (II) (10 g, 0.054 mol, 99.3 GC % by area) in methanol (100 ml) and the mixture was stirred at room temperature for 1 hour. Platinum on activated carbon (0.2 g, 5% Pt, dry) was subsequently added, the reaction vessel was flushed with nitrogen and pressurized to 6 bar with hydrogen at a maximum of 25° C. for 8 hours. The contents of the autoclave were filtered through Celite, washed with methanol and the solvent was distilled off under reduced pressure. N-(5-Chloro-2-isopropylbenzyl)cyclopropanamine (9.8 g, 96.8 GC-% by area, 78.0% of theory) was obtained as a light-yellow oil.

Platinum on activated carbon (5 g, 5% Pt, dry) was added to a solution of N-[(5-chloro-2-isopropylphenyl)methylene] cyclopropanamine (III) (160.8 g, 0.725 mol) in methanol (1350 ml). The reaction vessel was subsequently flushed with nitrogen and pressurized with 6 bar of hydrogen at a maximum of 25° C. for 8 hours. The contents of the autoclave were filtered through Celite, washed with methanol and the solvent was distilled off under reduced pressure. N-(5-Chloro-2-isopropylbenzyl)cyclopropanamine of the formula (I) (153.5 g, 97.1 GC-% by area, 91.9% of theory) was obtained as a light-yellow oil.

$^1$H-NMR (600 MHz, DMSO): δ=7.36 (d, 1H), 7.27 (d, 1H), 7.23 (dd, 1H), 3.76 (s, 2H), 3.23 (hept., 1H), 2.09 (m, 1H), 1.18 (s, 3H), 1.17 (s, 3H), 0.37 (m, 2H), 0.26 (m, 2H) ppm.

GC-MS: m/e=223 [M$^+$].

HPLC-MS: m/e=224 [M+H]$^+$.

The invention claimed is:

1. A compound, N-(5-Chloro-2-isopropylbenzyl)-cyclopropanamine of the formula (I)

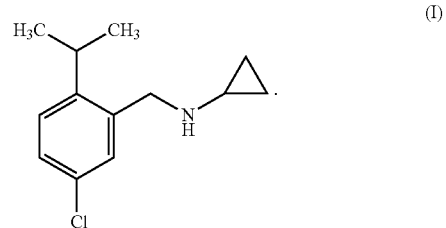

2. A process for preparing N-(5-chloro-2-isopropylbenzyl)-cyclopropanamine of the formula (I)

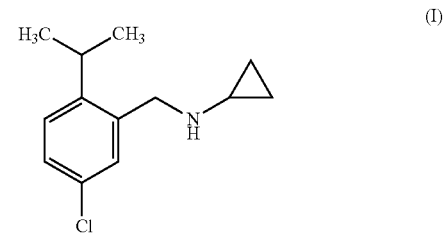

comprising the step of hydrogenating N-[(5-chloro-2-isopropylphenyl)methylene]cyclopropanamine of the formula (III)

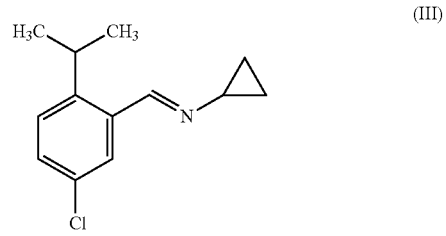

over a platinum catalyst.

3. A process according to claim 2, wherein N-[(5-chloro-2-isopropylphenyl)methylene]cyclopropanamine of the formula (III)

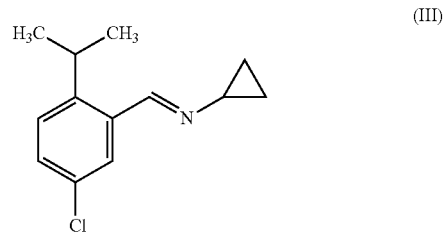

is prepared by the step of:
reacting 5-chloro-2-isopropylbenzaldehyde of the formula (II)

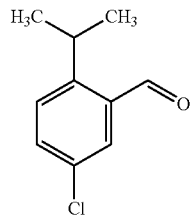
(II)

with cyclopropylamine.

4. A process according to claim 3, wherein 5-chloro-2-isopropylbenzaldehyde of the formula (II)

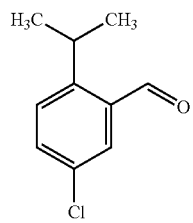
(II)

is prepared by the step of:
reacting the Grignard compound of the formula (V)

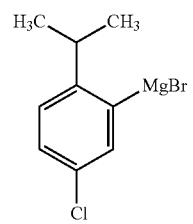
(V)

with a dialkylformamide of the formula (VI)

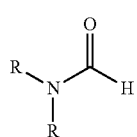
(VI)

where each R is a $C_1$-$C_4$-alkyl independently from the other.

5. A process according to claim 4, wherein the Grignard compound of the formula (V)

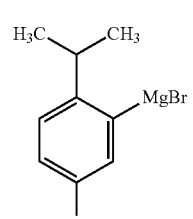
(V)

is prepared by the step of:
reacting 2-bromo-4-chloro-1-isopropylbenzene of the formula (IV)

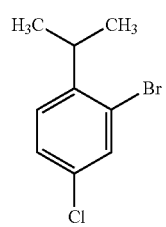
(IV)

with magnesium with selective insertion of the magnesium into the C—Br bond.

6. A compound 2-Bromo-4-chloro-1-isopropylbenzene of the formula (IV)

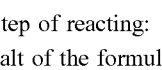
(IV)

7. A process for preparing 2-bromo-4-chloro-1-isopropylbenzene of the formula (IV)

(IV)

comprising the step of reacting:
a diazonium salt of the formula (IX)

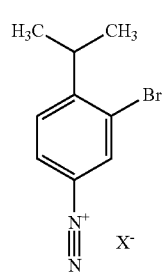
(IX)

where X is $HSO_4$, Cl, Br, $HCO_2$, $CH_3CO_2$ or $H_2PO_4$
with at least one of CuCl, $FeCl_2$ or $FeSO_4$ and also with at least one of aqueous HCl or metal chloride.

8. The process according to claim 7 wherein the diazonium salt of the formula (IX)

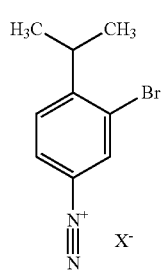
(IX)

is prepared by
reacting an ammonium salt of the formula (VIII)

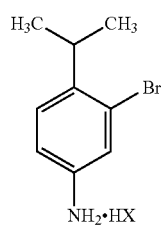
(VIII)

where X is $HSO_4$, Cl, Br, $HCO_2$, $CH_3CO_2$, or $H_2PO_4$ with at least one of $NaNO_2$ or $KNO_2$.

9. The process according to claim 8 wherein the ammonium salt of the formula (VIII)

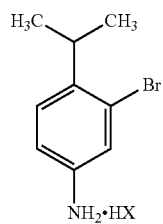
(VIII)

is prepared by
converting 3-bromo-4-isopropylaniline of the formula (VII)

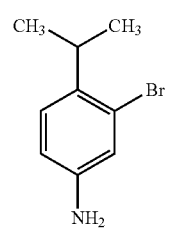
(VII)

by means of at least one acid.

10. The process according to claim 9 wherein 3-bromo-4-isopropylaniline of the formula (VII)

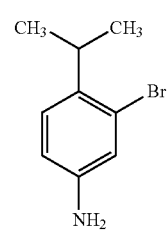
(VII)

is prepared by
reducing 2-bromo-1-isopropyl-4-nitrobenzene of the formula (XI)

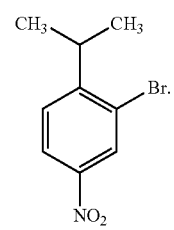
(XI)

11. The process according to claim 10 wherein 2-bromo-1-isopropyl-4-nitrobenzene of the formula (XI)

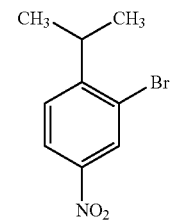
(XI)

is prepared by
bromination of p-nitrocumene of the formula (X)

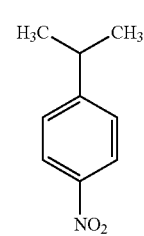
(X)

by means of dimethyldibromohydantoin in sulphuric acid.

12. The process according to claim 9 wherein the acid used to convert 3-bromo-4-isopropylaniline of the formula (VII) into the ammonium salts of the formula (VIII) is selected from the group consisting of $H_2SO_4$, HCl, $HCO_2H$, and $H_3PO_4$.

* * * * *